United States Patent
Narisada et al.

(10) Patent No.: US 6,842,233 B2
(45) Date of Patent: Jan. 11, 2005

(54) METHOD OF CLASSIFYING PARTICLES ON TWO-DIMENSIONAL FREQUENCY DISTRIBUTION MAP AND BLOOD ANALYZER UTILIZING THE SAME

(75) Inventors: Noriyuki Narisada, Akashi (JP); Hiroyuki Fujimoto, Kobe (JP); Yusuke Mori, Kobe (JP)

(73) Assignee: Sysmex Corporation, Hyogo (JP)

( * ) Notice: Subject to any disclaimer, the term of this patent is extended or adjusted under 35 U.S.C. 154(b) by 279 days.

(21) Appl. No.: 10/201,930

(22) Filed: Jul. 25, 2002

(65) Prior Publication Data

US 2003/0030784 A1 Feb. 13, 2003

(30) Foreign Application Priority Data

Jul. 26, 2001 (JP) .................................. 2001-226382

(51) Int. Cl.[7] .................. G01N 33/48; G01N 21/00; G06F 19/00
(52) U.S. Cl. ................ 356/39; 356/73; 356/335; 702/29; 702/30; 702/19
(58) Field of Search .................... 356/39, 73, 335, 356/336, 436; 702/29, 30, 31, 19, 45, 32; 382/128, 134

(56) References Cited

U.S. PATENT DOCUMENTS

| | | | | | |
|---|---|---|---|---|---|
| 4,661,913 A | * | 4/1987 | Wu et al. | ...................... | 702/19 |
| 5,325,169 A | * | 6/1994 | Nakamoto et al. | ............. | 356/73 |
| 5,690,105 A | * | 11/1997 | Shibata et al. | ............... | 600/300 |
| 5,721,433 A | * | 2/1998 | Kosaka | ........................ | 250/573 |
| 5,795,727 A | * | 8/1998 | Bierre et al. | ................ | 435/7.24 |
| 6,091,843 A | * | 7/2000 | Horesh et al. | ............... | 382/133 |
| 6,246,786 B1 | * | 6/2001 | Nishikiori et al. | ........... | 382/134 |
| 6,662,117 B2 | * | 12/2003 | Naito | .......................... | 702/29 |

FOREIGN PATENT DOCUMENTS

JP 2674705 B2 7/1997

* cited by examiner

Primary Examiner—Layla G. Lauchman
(74) Attorney, Agent, or Firm—Birch, Stewart, Kolasch & Birch, LLP (57) ABSTRACT

A method of classifying particles indicated on a two-dimensional frequency distribution map into particle clusters, includes the steps of: dividing the particles into a first cluster and a second cluster by a line containing a mode coordinate of the particles, presuming a third cluster so that the first and third clusters are symmetrical with respect to the mode coordinate, calculating variance and covariance of a cluster including the first and third clusters to obtain an ellipse region surrounding the first and third clusters based on the calculated variance and covariance, and determining the particles in the obtained ellipse region as a particle cluster.

18 Claims, 12 Drawing Sheets

METHOD OF CLASSIFYING PARTICLES ON TWO-DIMENSIONAL FREQUENCY DISTRIBUTION MAP AND BLOOD ANALYZER UTILIZING THE SAME

CROSS-REFERENCE TO RELATED APPLICATION

This application is related to Japanese Patent Application No. 2001-226382 filed on Jul. 26, 2001, whose priority is claimed under 35 USC § 119, the disclosure of which is incorporated by reference in its entirety.

BACKGROUND OF THE INVENTION

1. Field of the Invention

The present invention relates to a method of classifying particles on a two-dimensional frequency distribution map and a blood analyzer utilizing the same. In particular, it relates to a method and an apparatus for classifying mature blood cells and immature blood cells contained in blood on the two-dimensional frequency distribution map.

2. Description of Related Art

As the above-mentioned method, conventionally known is a method of classifying mature erythrocytes and reticulocytes contained in blood on a one-dimensional frequency distribution map into two particle clusters by obtaining a distribution peak on the one-dimensional frequency distribution map, setting a threshold value of the frequency in accordance with the peak and determining the two clusters by the threshold value (for example, see Japanese Examined Patent Publication No. 2674705).

SUMMARY OF THE INVENTION

An object of the present invention is to improve accuracy in classifying particles indicated on a two-dimensional distribution map.

The present invention provides a method of classifying particles indicated on a two-dimensional frequency distribution map into particle clusters, comprising the steps of: dividing the particles into a first cluster and a second cluster by a line containing a mode coordinate of the particles, presuming a third cluster so that the first and third clusters are symmetrical with respect to the mode coordinate, calculating variance and covariance of a cluster including the first and third clusters to obtain an ellipse region surrounding the first and third clusters based on the calculated variance and covariance, and determining the particles in the obtained ellipse region as a particle cluster.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

A method of the present invention for classifying particles indicated on a two-dimensional frequency distribution map into particle clusters, includes the steps of: dividing the particles into a first cluster and a second cluster by a line containing a mode coordinate of the particles, presuming a third cluster so that the first and third clusters are symmetrical with respect to the mode coordinate, calculating variance and covariance of a cluster including the first and third clusters to obtain an ellipse region surrounding the first and third clusters based on the calculated variance and covariance, and determining the particles in the obtained ellipse region as a particle cluster.

According to the present invention, the particles may include blood cells and the two-dimensional distribution map may indicate a particle cluster including mature granulocytes and immature granulocytes of leukocytes or a particle cluster including mature erythrocytes and reticulocytes. In this cases, a cluster of mature granulocytes or a cluster of mature erythrocytes can be classified by the ellipse region calculated by the method of the invention.

In the case of classifying the mature granulocytes and the immature granulocytes of the leukocytes, the two-dimensional distribution map may be a scattergram based on a side fluorescent light intensity and a side scattered light intensity detected by using a flow cytometer from a sample containing leukocytes which have been subjected to nucleic acid staining.

Further, in the case of classifying the mature erythrocytes and the reticulocytes, may be used as the distribution map a scattergram based on the side fluorescent light intensity and the forward scattered light intensity detected by using the flow cytometer from a sample containing erythrocytes which have been subjected to fluorescent staining.

The present invention further provides a blood analyzer which analyzes blood by utilizing the above-described fractioning method.

In another aspect, the present invention provides a blood analyzer comprising: a detecting section for detecting characteristic parameters of particles contained in blood, a distribution map preparing section for preparing a two-dimensional frequency distribution map of the particles based on the detected parameters, and a classifying section for classifying the particles on the distribution map, wherein the classifying section carries out the steps of: dividing the particles into a first cluster and a second cluster by a line containing a mode coordinate of the particles; presuming a third cluster so that the first and third clusters are symmetrical with respect to the mode coordinate; calculating variance and covariance of a cluster including the first and third clusters to obtain an ellipse region surrounding the first and third clusters based on the calculated variance and covariance; and determining the particles in the obtained ellipse region as a particle cluster.

Hereinafter, the present invention is detailed by way of an embodiment with reference to FIGS. 1 to 14 of the drawings. Components which are common in the figures are indicated with common reference numerals.

Structure of a Blood Analyzer

Figure 1:
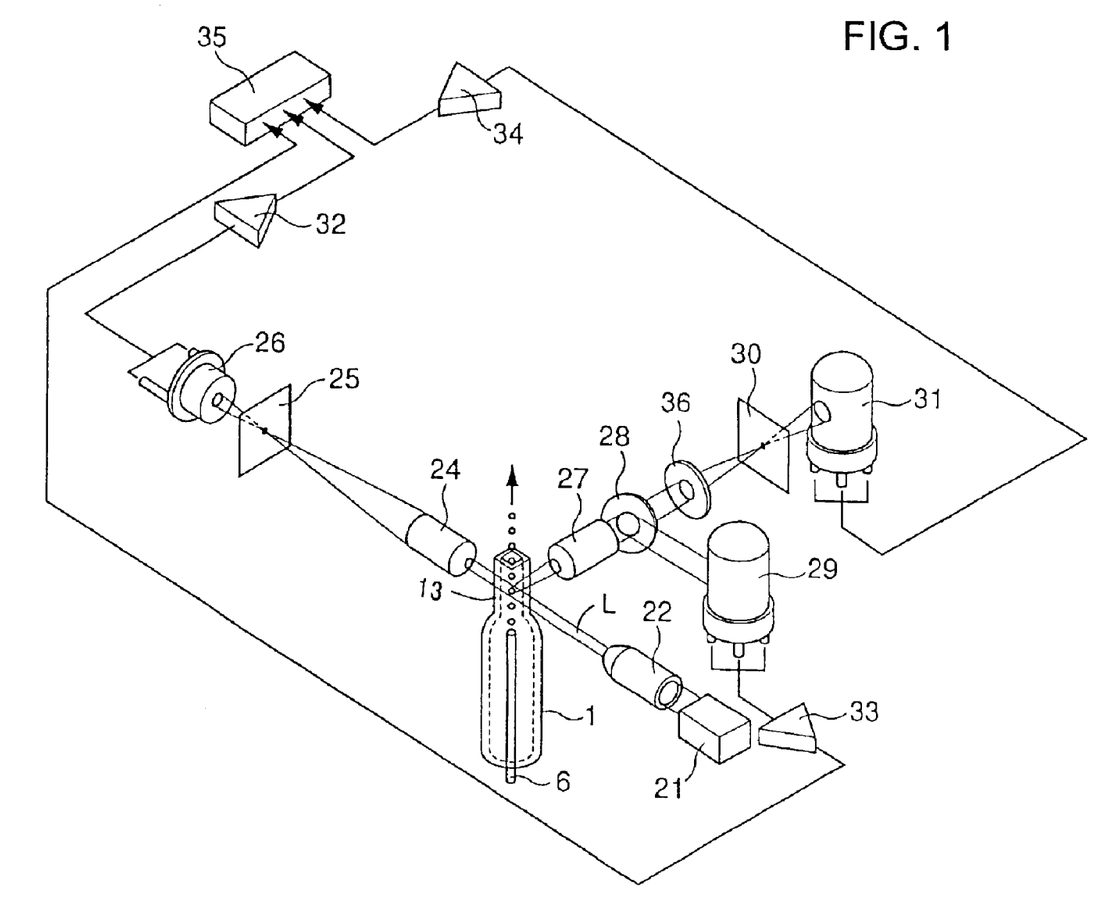
FIG. 1 is a perspective view illustrating an optical system according to an embodiment of the present invention.

FIG. 1 is a perspective view illustrating an optical system; i.e., a flow cytometer of the blood analyzer according to the present invention. Referring to FIG. 1 a nozzle 6 discharges a sample liquid containing blood cells toward an orifice 13 in a sheath flow cell 1. A laser beam L output from a laser diode 21 irradiates the orifice 13 of the sheath flow cell 1 via a collimate lens 22. Forward scattered light emitted from the blood cells passing through the orifice 13 enters a photodiode 26 via a condenser lens 24 and a pinhole plate 25.

On the other hand, side scattered light emitted from the blood cells passing through the orifice 13 enters a photomultiplier tube 29 via a condenser lens 27 and a dichroic mirror 28. Further, side fluorescent light emitted from the blood cells passing through the orifice 13 enters a photomultiplier tube 31 via the condenser lens 27, the dichroic mirror 28, a filter 36 and a pinhole plate 30.

A forward scattered light signal output from the photodiode 26, a side scattered light signal output from the photomultiplier tube 29 and a side fluorescent light signal output from the photomultiplier tube 31 are amplified by amplifiers 32, 33 and 34, respectively, and input to an analysis section 35.

Figure 2:
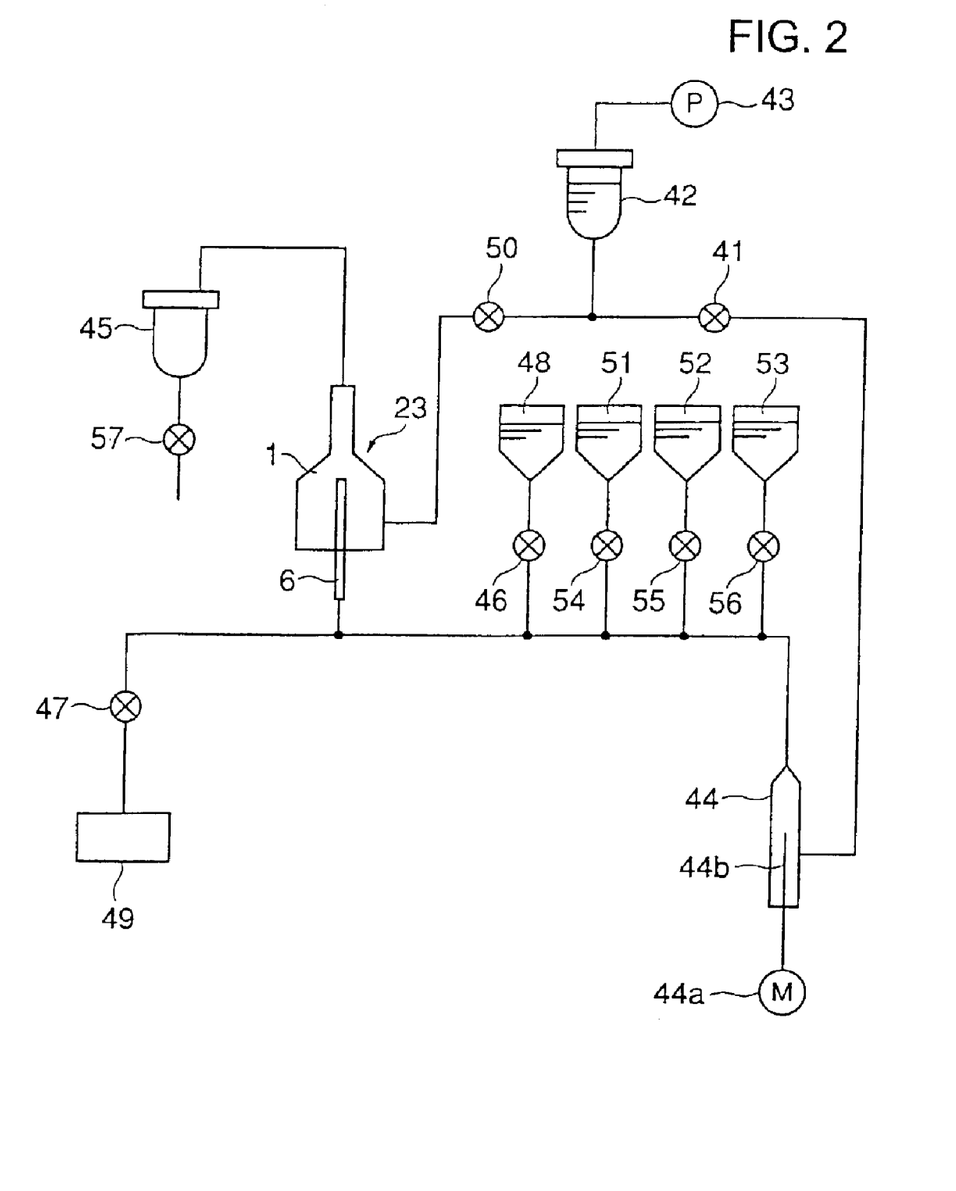
FIG. 2 is a block diagram illustrating a fluid system according to the embodiment of the present invention.

FIG. 2 is a block diagram illustrating a fluid system of the blood analyzer shown in FIG. 1. First, in a washing process, valves 41 and 50 are opened to feed a sheath liquid out of a sheath liquid chamber 42 under a positive pressure applied by a pressurizing device 43. Then, the sheath liquid passes through the valve 41, a quantifying syringe 44 and the nozzle 6 to a drain chamber 45. The sheath liquid also passes through the valve 50 and the cell 1 to the drain chamber 45. The valves 41 and 50 are closed after a predetermined period of time. Thus, the quantifying syringe 44, the nozzle 6, the cell 1 and paths connecting them are washed with the sheath liquid.

In a measurement process, valves 46 and 47 are opened to suck a blood-containing sample liquid under a negative pressure applied by a suction device 49 out of a reaction chamber 48 in which the sample liquid is reacted with a reagent. When the path between the valve 46 and the nozzle 6 is filled with the sample liquid, the valves 46 and 47 are closed. Then, the valve 50 is opened, thereby the sheath liquid is fed from the sheath liquid chamber 42 to the cell 1 under the positive pressure applied by the pressurizing device 43 and drained into the drain chamber 45.

When the valve 41 is opened, the pressure applied by the pressurizing device 43 is transmitted to the tip of the nozzle 6 via the quantifying syringe 44. Thereby, the pressure of the sheath liquid outside the nozzle and that of the sheath liquid inside the nozzle are balanced at the tip of the nozzle 6. When a piston 44b of the quantifying syringe 44 is driven by a motor 44a in this state, the sample liquid existing between the valve 46 and the nozzle 6 is easily discharged from the nozzle 6 to the orifice 13 and narrowed by the sheath liquid to pass through the orifice 13. The sample liquid is then drained into the drain chamber 45 together with the sheath liquid.

Then, the piston 44b of the quantifying syringe 44 is stopped to finish the measurement process.

Subsequently, the motor 44a is driven in a reverse direction to put the piston 44b back, thereby the quantifying syringe 44 returns to an initial state. During this procedure, the valves 41 and 50 are opened so that the above-mentioned washing process is carried out to get ready for the next measurement process.

The sample liquids contained in the other reaction chambers 51, 52 and 53, respectively, are also measured in sequence by opening and closing valves 54, 55 and 56 in the same manner as the above-described process.

A valve 57 functions to empty the drain chamber 45, so that it is opened and closed as needed.

Figure 3:
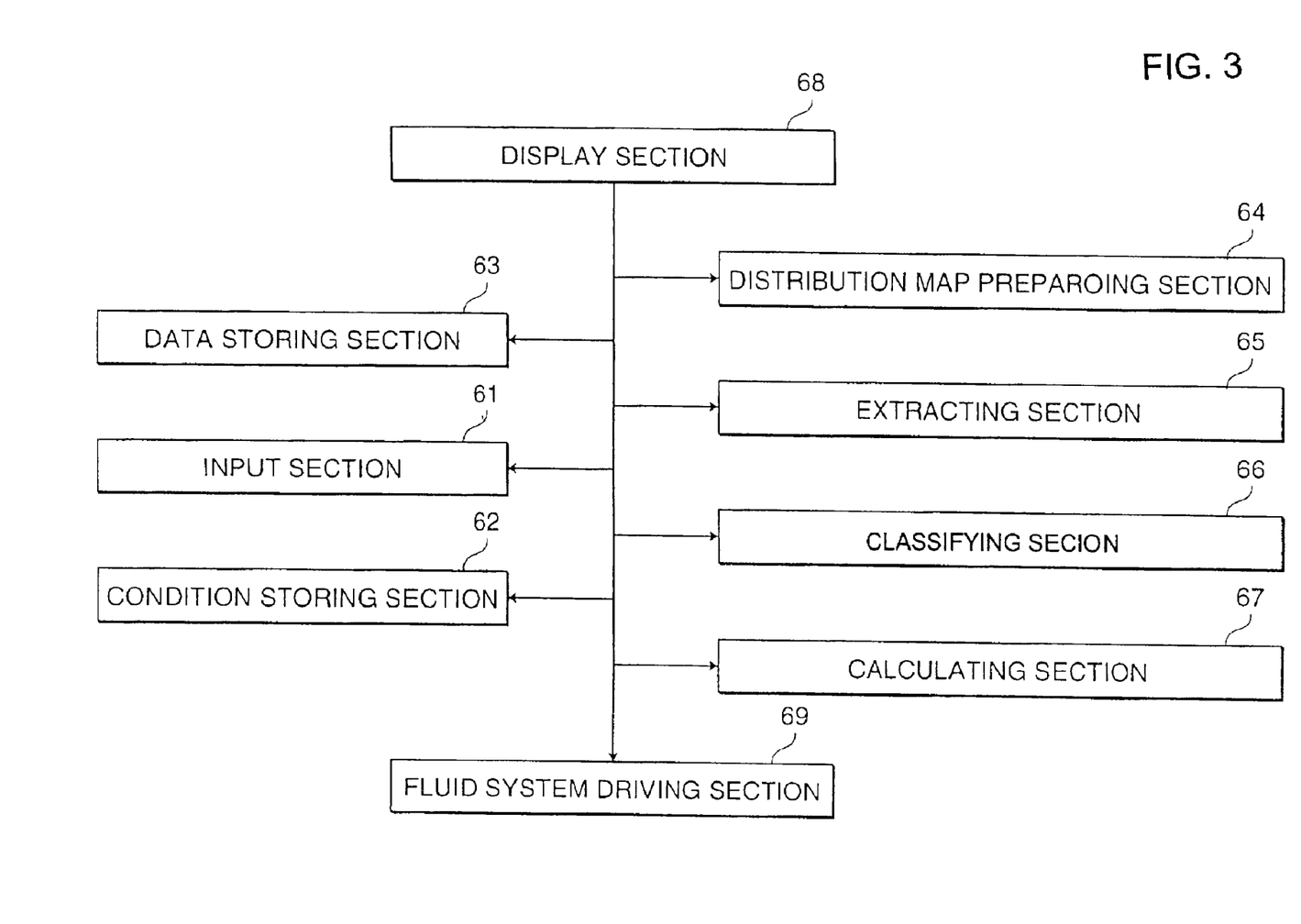
FIG. 3 is a block diagram illustrating a structure of an analysis section according to the embodiment of the present invention.

FIG. 3 is a block diagram illustrating the structure of the analysis section 35 shown in FIG. 1. Referring to FIG. 3, an input section 61 inputs data for previously setting up conditions such as numeric values and regions. For example, the input section 61 is a keyboard or a mouse.

A condition storing section 62 stores the given conditions and a data storing section 63 stores optical data obtained from the signals output from the photodiode 26 and the photomultiplier tubes 29 and 31. A distribution map preparing section 64 prepares a two-dimensional frequency distribution map (scattergram) based on the optical data stored in the data storing section 63, i.e., two parameters out of a forward scattered light intensity (Fsc), a side scattered light intensity (Ssc) and a side fluorescent light intensity (Sfl). An extracting section 65 extracts coordinates and regions from the distribution map prepared by the distribution map preparing section 64.

A classifying section 66 determines classification regions of particles on the distribution map prepared by the distribution map preparing section 64. A calculating section 67 counts the number of the particles in the classification regions. The calculation results obtained by the calculating section 67 are displayed in a display section 68 together with the distribution map prepared by the distribution map preparing section 64. Further, a fluid system driving section 69 drives the valves 41, 46, 47, 50, 54, 55, 56 and 57 and the motor 44a shown in FIG. 2. The analysis section 35 is constituted by consisted of a personal computer.

Preparation of Two-dimensional Frequency Distribution Maps Depending on a sample, one measurement mode is selected at the input section 61 out of four measurement modes: a nucleated erythrocyte measurement mode; a leukocyte/basophil measurement mode; a leukocyte 4-part differential measurement mode; and a reticulocyte measurement mode. In accordance with the selected mode, blood quantified by a blood quantifying section (not shown) and reagents such as a diluent, a stain solution and a hemolytic agent are contained in the corresponding one of reaction chambers 48, 51, 52 and 53 and the blood is subjected to a predetermined treatment. Blood samples are thus prepared and measured in the sheath row cell 1 in sequence.

In the nucleated erythrocyte measurement mode, blood of 18 μl and Stromatolyzer NR hemolytic agent (manufactured by Sysmex Corporation) of 882 μl are introduced in the reaction chamber 48. Then, Stromatolyzer NR fluorescent stain solution (manufactured by Sysmex Corporation) of 18 µl is added. The reaction is continued in this state for about 7 seconds to hemolyze erythrocytes and stain leukocytes and nucleated erythrocytes.

Figure 4:
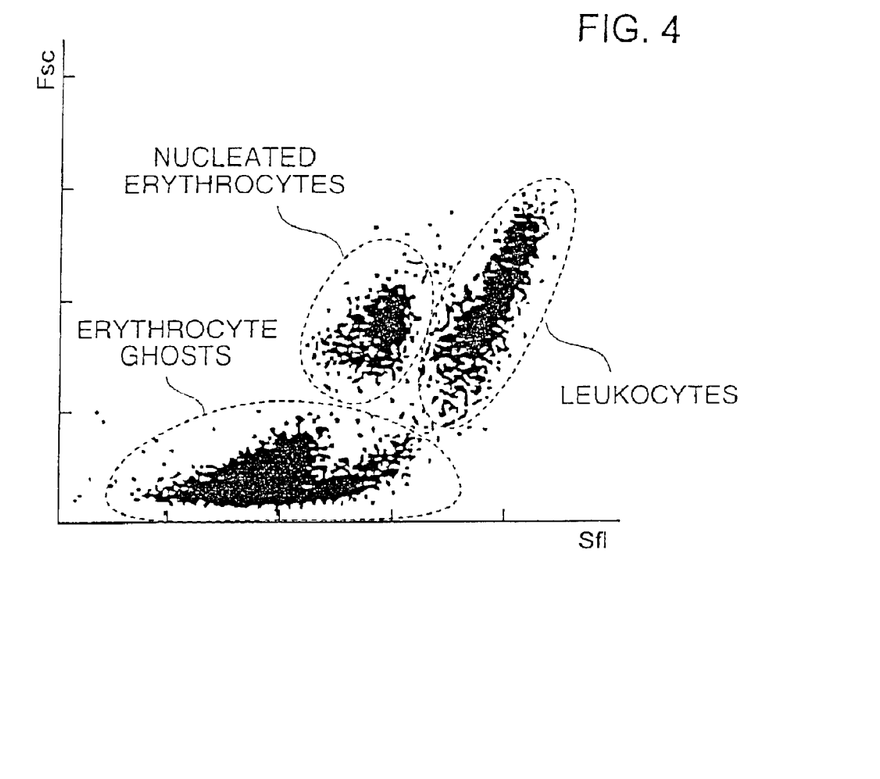
FIG. 4 is an example of a distribution map according to the embodiment of the present invention.

The thus treated sample is discharged from the nozzle 6 by the quantifying syringe 44. Among data obtained by the optical measurement, a side fluorescent light intensity (Sf1) and a forward scattered light intensity (Fsc) are used to prepare a two-dimensional frequency distribution map of FIG. 4. In FIG. 4, the nucleated erythrocytes, the erythrocytes and the leukocytes appear in expected appearance regions encircled with broken lines, respectively.

In the leukocyte/basophil measurement mode, blood of 18 µl and Stromatolyzer FB (II) (manufactured by Sysmex Corporation) of 882 µl are introduced in the reaction chamber 51. The reaction is continued in this state for about 14 seconds, thereby the erythrocytes are hemolyzed and the nuclei of the leukocytes other than the basophils are exposed and shrunk.

Figure 5:
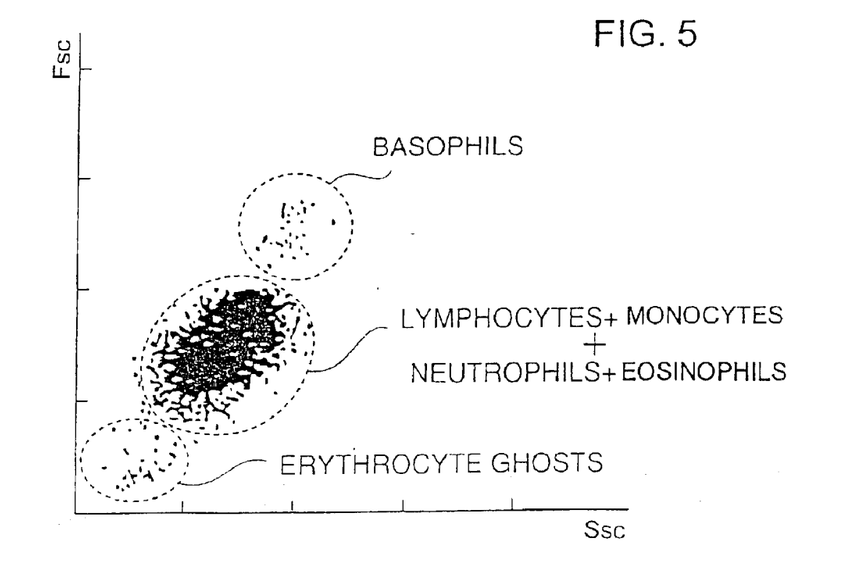
FIG. 5 is an example of a distribution map according to the embodiment of the present invention.

The thus treated sample is discharged from the nozzle 6 by the quantifying syringe 44. Among data obtained by the optical measurement, a side scattered light intensity (Ssc) and a forward scattered light intensity (Fsc) are used to prepare a two-dimensional frequency distribution map of FIG. 5. In FIG. 5, regions encircled with respective broken lines are expected appearance regions of the basophils and the other leukocytes (lymphocytes, monocytes, neutrophils and eosinophils).

In the leukocyte 4-part differential measurement mode, blood of 18 µl and Stromatolyzer 4DL hemolytic agent (manufactured by Sysmex Corporation) of 882 µl are introduced in the reaction chamber 52. Then, Stromatolyzer 4DS fluorescent stain solution (manufactured by Sysmex Corporation) of 18 µl is added. The reaction is continued in this state for about 22 seconds to hemolyze the erythrocytes and stain the leukocytes.

Figure 6:
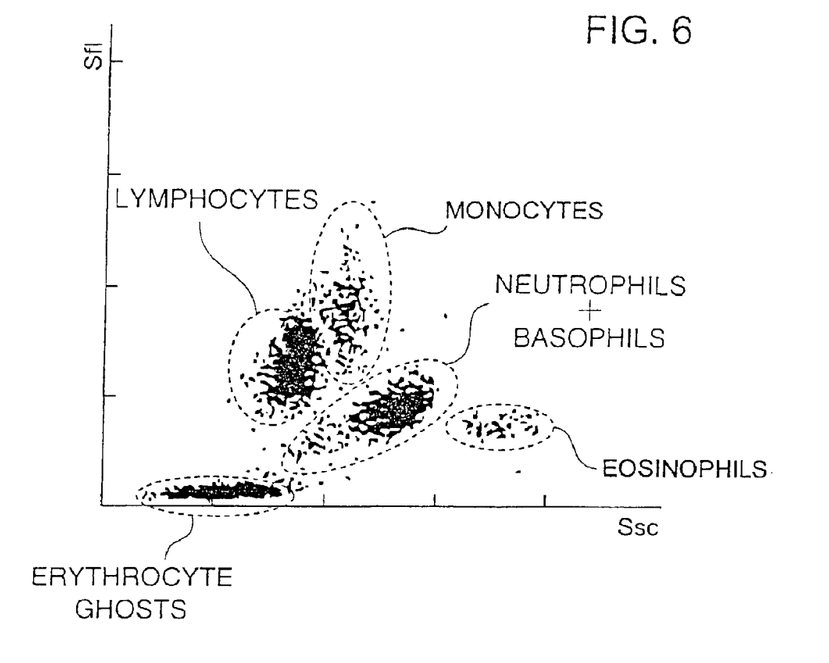
FIG. 6 is an example of a distribution map according to the embodiment of the present invention.

The thus treated blood sample is discharged from the nozzle 6 by the quantifying syringe 44. Among data obtained by the optical measurement, a side scattered light intensity (Ssc) and a side fluorescent light intensity (Sf1) are used to prepare a two-dimensional frequency distribution map of FIG. 6. In FIG. 6, a cluster of lymphocytes, a cluster of monocytes, a cluster of neutrophils and basophils and a cluster of eosinophils correspond with the expected regions encircled with respective broken lines.

In the reticulocyte measurement mode, blood of 4.5 µl and Retsearch (II) diluent (manufactured by Sysmex Corporation) of 895.5 µl are introduced in the reaction chamber 53. Then, Retsearch (II) fluorescent stain solution (manufactured by Sysmex Corporation) of 18 µl is added. The reaction is continued in this state for 31 seconds to stain the reticulocytes and the like.

Figure 7:
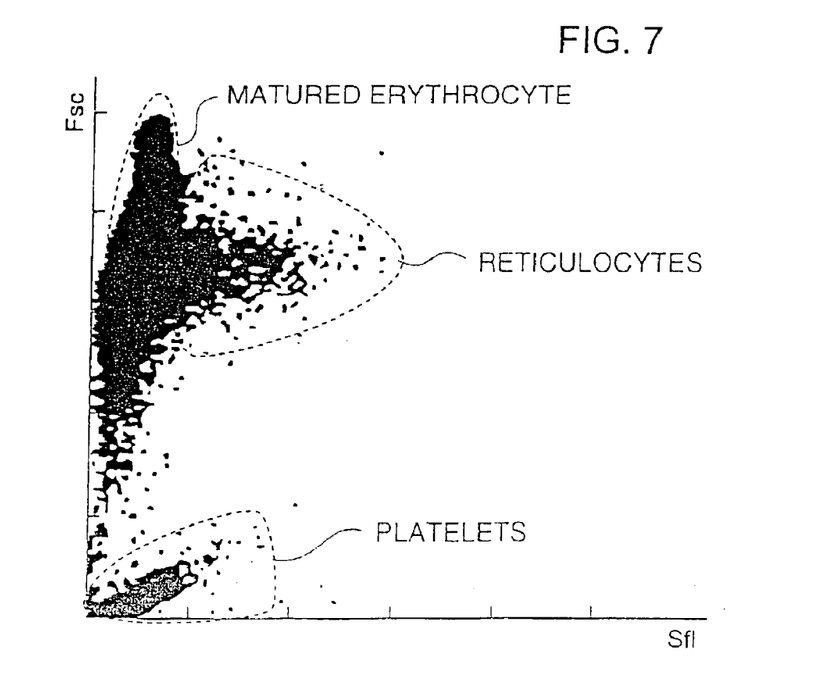
FIG. 7 is an example of a distribution map according to the embodiment of the present invention.

The thus treated blood sample is discharged from the nozzle 6 by the quantifying syringe 44. Among data obtained by the optical measurement, a side fluorescent light intensity (Sf1) and a forward scattered light intensity (Fsc) are used to prepare a two-dimensional frequency distribution map of FIG. 7. In FIG. 7, a cluster of reticulocytes, a cluster of mature erythrocytes and a cluster of platelets correspond with the expected regions encircled with respective broken lines.

Classification Process

Figure 8:
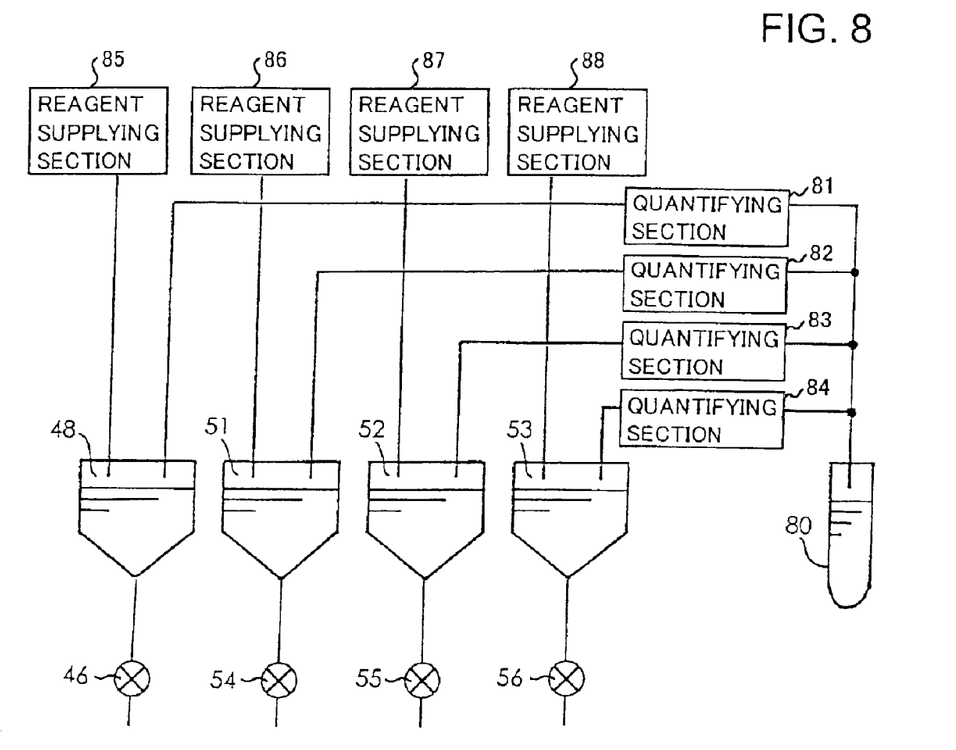
FIG. 8 is an example of a distribution map according to the embodiment of the present invention.

Leukocytes can be classified into lymphocytes, monocytes, neutrophils, basophils and eosinophils. In the leukocyte 4-part differential measurement mode, they are scattered on the distribution map as shown in FIG. 6. If the blood sample is an abnormal sample containing immature granulocytes such as immature neutrophils, a two-dimensional frequency distribution map corresponding to FIG. 6 is obtained as shown in FIG. 8. That is, the immature neutrophils appear not below but above a cluster of neutrophils and basophils in contact with the cluster.

Figure 9:
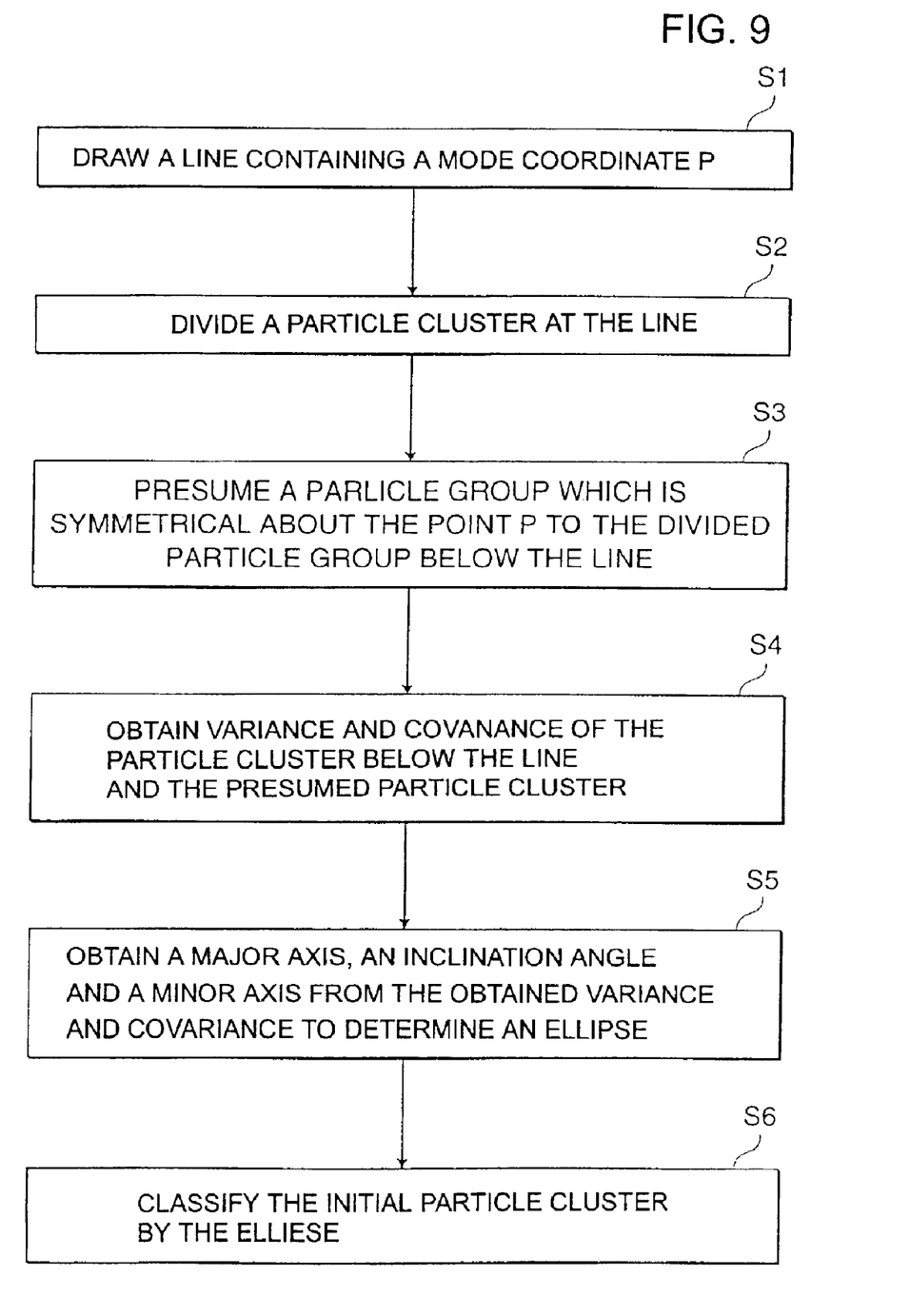
FIG. 9 is a flow chart illustrating the classifying steps according to the embodiment of the present invention.

Then, the classifying section 66 (FIG. 3) accurately determines a cluster of neutrophils and basophils and a cluster of immature neutrophils in accordance with the flow chart shown in FIG. 9.

Figure 10:
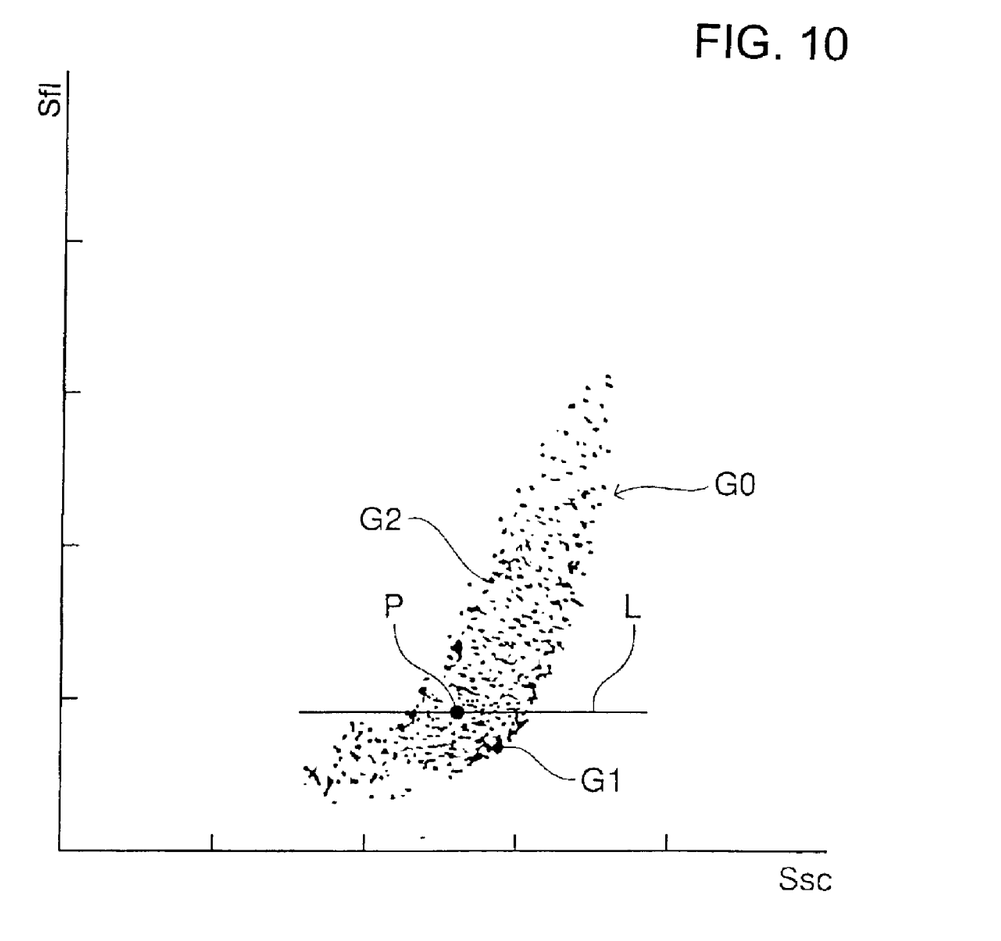
FIG. 10 is an example of a distribution map used in the embodiment of the present invention.

First, as shown in FIG. 10, a line L containing a mode coordinate P of a target particle cluster G0 is drawn (step S1). Then, the target particle cluster is divided into a first particle cluster G1 below the line L and a second particle cluster G2 above the line L (step S2). It is considered that the first particle cluster G1 does not include the immature neutrophils but includes only normal particles which are normally distributed therein.

Figure 11:
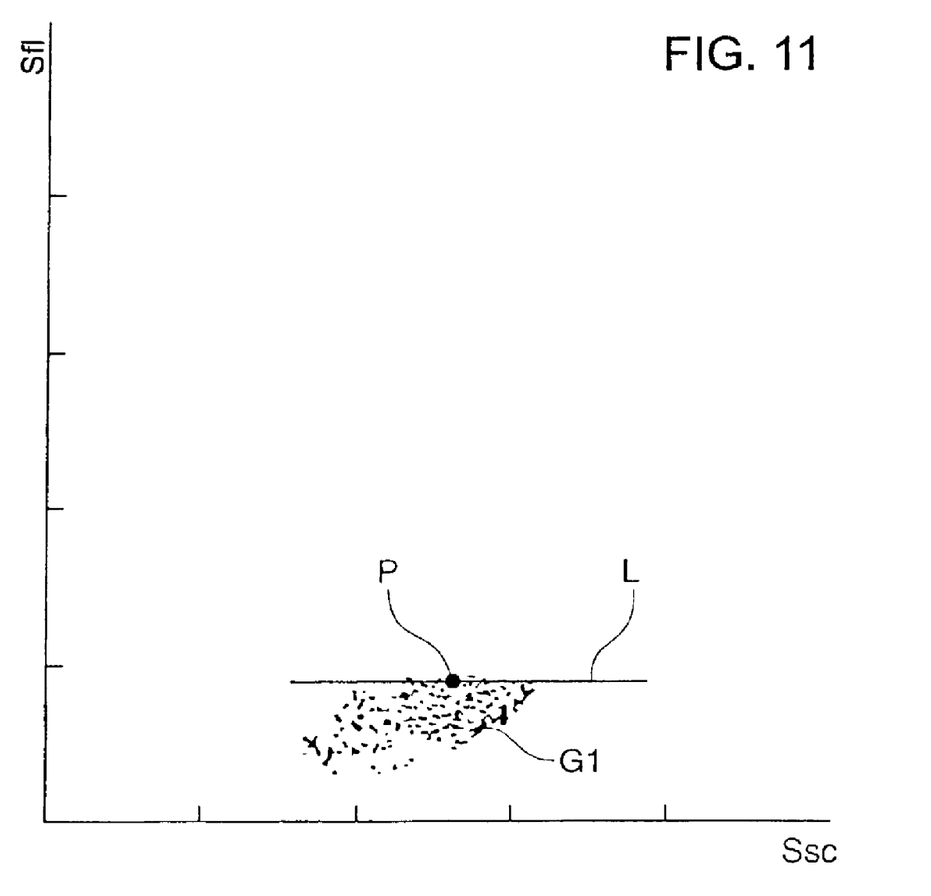
FIG. 11 is an example of a distribution map used in the embodiment of the present invention.
Figure 12:
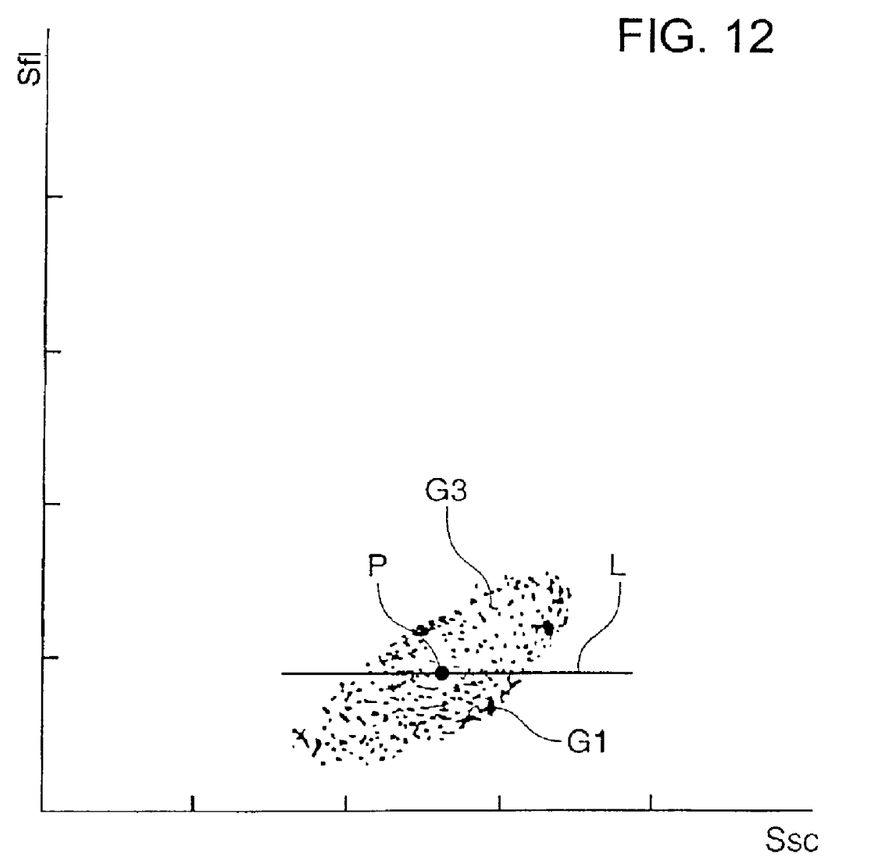
FIG. 12 is an example of a distribution map used in the embodiment of the present invention.

Then, as shown in FIG. 11, attention is paid only to the first particle cluster G1 below the line L and a third particle cluster G3 which is symmetrical about the point P to the first particle cluster G1 is presumed (step S3). The third particle cluster G3 is presumed to be a cluster which does not include the immature neutrophils, because the clusters G1 and G3 are symmetrical about the point P and the cluster G1 does not include the immature neutrophils.

Subsequently, on the assumption that a cluster including the first and third particle clusters G1 and G3 is normally distributed, variance and covariance thereof are obtained (step S4).

Figure 13:
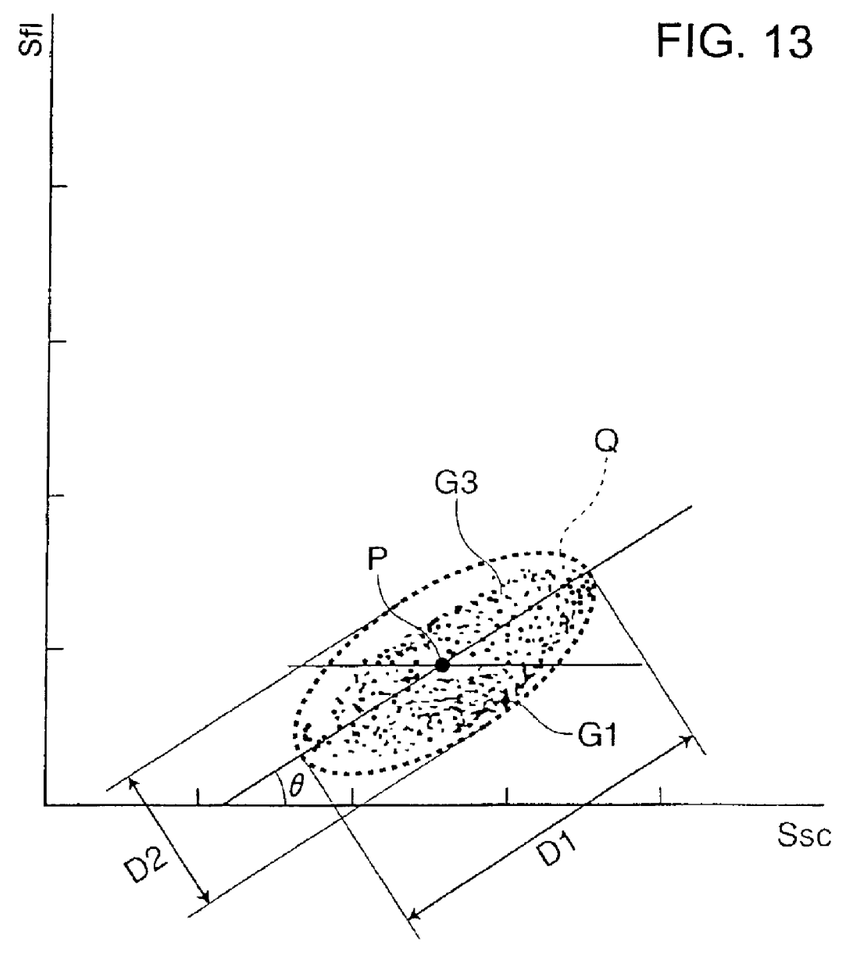
FIG. 13 is an example of a distribution map used in the embodiment of the present invention.

Then, as shown in FIG. 13, a major axis D1, an inclination angle θ and a minor axis D2 of an ellipse Q surrounding the clusters G1 and G3 are calculated from the variance and the covariance to determine an expression of the ellipse Q on coordinates of the distribution map (step S5).

Figure 14:
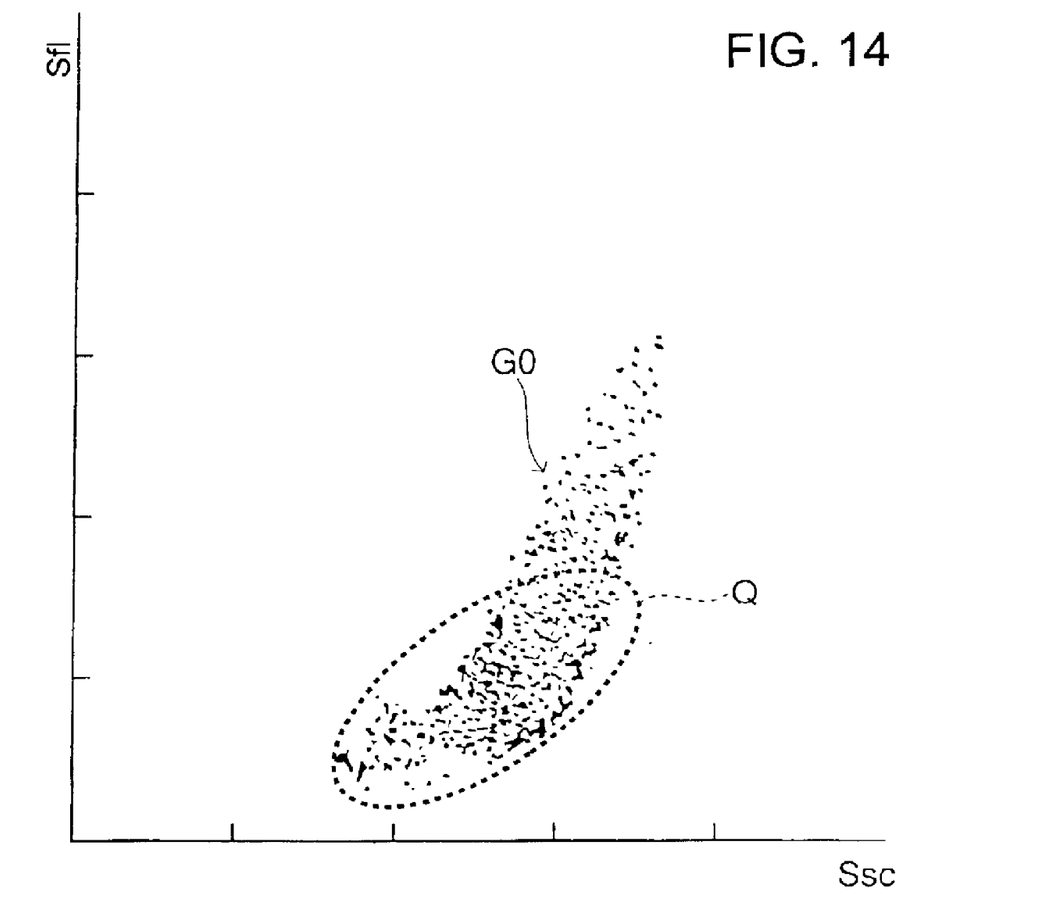
FIG. 14 is an example of a distribution map used in the embodiment of the present invention.

Then, as shown in FIG. 14, the initial particle cluster G0 is cut off by the thus determined ellipse Q (step S6). Then, the calculating section 67 (FIG. 3) counts the particles within the ellipse Q as the neutrophils and the basophils and those outside the ellipse Q as the immature neutrophils. The count results are displayed in the display section 68.

The method of determining the ellipse Q shown in FIG. 13 is described below.

Provided that the point P is on the coordinates $(P_1, P_2)$, the variance in the direction of the major axis of the ellipse Q is $V_L$, the variance in the direction of the minor axis of the ellipse Q is $V_S$ and optional coordinates on the distribution map are $(X, Y)$, the ellipse Q satisfies the following equation:

$$(X-P_1)^2/V_L + (Y-P_2)^2/V_S = C \ (C \text{ is a fixed value})$$

The left side of the equation defines a ratio between the major axis and the minor axis and an inclination angle of the ellipse Q. A size of the ellipse Q is suitably determined by the fixed value C.

In the above-described classification process, a cluster existing in a position symmetrical about the point P to the first particle cluster G1 is presumed as the third particle cluster G3. Therefore, regardless of the angle of the particle cluster G0 with respect to the line L, the cluster G3 can be always presumed as a cluster equivalent to the cluster G1. As a result, the particle cluster including the clusters G1 and G3 can be assumed to be normally distributed, which allows accurate classification.

Further, the above-described classifying method can also be adopted to classify the mature erythrocytes and the immature erythrocytes shown in FIG. 7.

According to the present invention, two particle clusters which are not clearly distinguished physiologically or morphologically, such as mature granulocytes and immature granulocytes contained in blood, can accurately be classified on a two-dimensional distribution map. Even in the case where the distribution of such particle clusters is variable depending on the sample, for example, the inclination of the clusters easily fluctuates, the classification can be carried out accurately.

What is claimed is:

1. A method of classifying particles indicated on a two-dimensional frequency distribution map into particle clusters, comprising the steps of:
   dividing the particles into a first cluster and a second cluster by a line containing a mode coordinate of the particles;
   presuming a third cluster so that the first and third clusters are symmetrical with respect to the mode coordinate;
   calculating variance and covariance of a cluster including the first and third clusters to obtain an ellipse region surrounding the first and third clusters based on the calculated variance and covariance; and
   determining the particles in the obtained ellipse region as a particle cluster.

2. A method according to claim 1, wherein the particles include blood cells and the particles indicated on the two-dimensional distribution map include mature granulocytes and immature granulocytes of leukocytes.

3. A method according to claim 2, wherein the determined particle cluster is a cluster of mature granulocytes.

4. A method according to claim 2, wherein the two-dimensional frequency distribution map is a scattergram based on a side fluorescent light intensity and a side scattered light intensity detected by using a flow cytometer from a sample containing leukocytes which have been subjected to nucleic acid staining.

5. A blood analyzer which analyzes blood by utilizing a method according to claim 1.

6. A blood analyzer comprising: a detecting section for detecting characteristic parameters of particles contained in blood, a distribution map preparing section for preparing a two-dimensional frequency distribution map of the particles based on the detected parameters, and a classifying section for classifying the particles on the distribution map,
   by dividing the particles into a first cluster and a second cluster by a line containing a mode coordinate of the particles;
   defining a third cluster symmetrical to the first cluster with respect to the mode coordinate;
   calculating variance and covariance of a fourth cluster including the first and third clusters to obtain an ellipse region surrounding the first and third clusters based on the calculated variance and covariance; and
   determining the particles in the obtained ellipse region as a particle cluster.

7. A blood analyzer according to claim 6, wherein the particles indicated on the two-dimensional distribution map includes mature granulocytes and immature granulocytes of leukocytes.

8. A blood analyzer according to claim 7, wherein the determined particle cluster is a cluster of mature granulocytes.

9. A blood analyzer according to claim 6, wherein the detecting section includes a flow cytometer and the characteristic parameters include a side fluorescent light intensity and a side scattered light intensity detected by the flow cytometer.

10. A blood analyzer according to claim 6, wherein the particles include leukocytes which have been subjected to nucleic acid staining.

11. A method of classifying a two-dimensional frequency distribution of particles into particle clusters, comprising the steps of:
   assigning particles on a first side of a line containing a mode coordinate of the particles to a first cluster;
   assigning particles on a second side of the line to a second cluster;
   defining a third cluster symmetrical to the first cluster with respect to the mode coordinate; and
   calculating variance and covariance of a fourth cluster including the first and third clusters to obtain an ellipse region surrounding the first and third clusters based on the calculated variance and covariance.

12. The method of claim 11 including the additional step of defining a fifth cluster comprising the particles in the ellipse region.

13. The method of claim 11, wherein the particles include blood cells and the particles represented by the two-dimensional frequency distribution include mature granulocytes and immature granulocytes of leukocytes.

14. The method of claim 12, wherein the fifth cluster is a cluster of mature granulocytes.

15. A method according to claim 14, wherein the two-dimensional frequency distribution comprises a scattergram based on a side fluorescent light intensity and a side scattered light intensity detected by using a flow cytometer from a sample containing leukocytes which have been subjected to nucleic acid staining.

16. A blood analyzer comprising:
   a detector for detecting characteristic parameters of particles contained in blood; and
   a processor for preparing a two-dimensional frequency distribution of the particles based on the detected parameters, assigning particles on a first side of a line containing a mode coordinate of the particles to a first cluster, assigning particles on a second side of the line to a second cluster, defining a third cluster symmetrical to the first cluster with respect to the mode coordinate, and calculating variance and covariance of a fourth cluster including the first and third clusters to obtain an ellipse region surrounding the first and third clusters based on the calculated variance and covariance.

17. A method of classifying a two-dimensional frequency distribution of particles into particle clusters, comprising the steps of:
   assigning particles on a first side of a line to a first cluster, the line based on a frequency distribution of the particles;
   assigning particles on a second side of the line to a second cluster;
   defining a third cluster based on the first cluster; and
   defining a fourth cluster including the first and third clusters.

18. A blood analyzer comprising:
   a detector for detecting characteristic parameters of particles contained in blood; and
   a processor for preparing a two-dimensional frequency distribution of the particles based on the detected parameters, assigning particles on a first side of a line to a first cluster, assigning particles on a second side of the line to a second cluster, defining a third cluster based on the first cluster, and defining a fourth cluster including the first and third clusters, the line based on a frequency distribution of the particles.

* * * * *